United States Patent
Vyas et al.

(10) Patent No.: US 6,245,908 B1
(45) Date of Patent: Jun. 12, 2001

(54) PROCESS FOR PREPARING CARBAMAZEPINE FROM IMINOSTILBENE

(75) Inventors: Ketan Dhansukhlal Vyas; Wajid Sajjad Jafri; Ashok Krishna Kulkarni, all of Mysore (IN)

(73) Assignee: Max India Limited, Punjub (IN)

( * ) Notice: Subject to any disclaimer, the term of this patent is extended or adjusted under 35 U.S.C. 154(b) by 0 days.

(21) Appl. No.: 09/253,583

(22) Filed: Feb. 19, 1999

(30) Foreign Application Priority Data

Nov. 16, 1998 (IN) ........................................ 3427/98

(51) Int. Cl.$^7$ ................................................ C07D 223/18
(52) U.S. Cl. ............................................... 540/589
(58) Field of Search ............................................. 540/589

(56) References Cited

U.S. PATENT DOCUMENTS 5,043,444 * 8/1991 Mullner et al. ...................... 544/169
5,183,903 * 2/1993 Welstead, Jr. et al. .............. 548/952

FOREIGN PATENT DOCUMENTS

| 41 11 922 | * 10/1992 | (DE) . |
| 43 07 181 | * 11/1994 | (DE) . |
| 44 21 294 | * 12/1995 | (DE) . |
| WO 98/04549 | * 2/1998 | (WO) . |

OTHER PUBLICATIONS

Ahmad et al. (Indian J. Chem., Sect. B (1988), 27B(6), 583) Abstract.*

Haasz et al. (HU 63389) Abstract, 1993.*

Troyanskii et al. (Izv. Akad. Nauk SSSR, Ser. Khim. (1985), (11), 2537–46) Abstract.*

* cited by examiner

Primary Examiner—Bruck Kifle
(74) Attorney, Agent, or Firm—Ladas & Parry

(57) ABSTRACT

A process for preparing carbamazepine from iminostilbene is disclosed. The iminostilbene is reacted with urea in a protonating medium. This process results in improvements over prior art processes involving iminostilbene. Carbamazepine is a known muscle relaxant, anticonvulsant and antidepressant drug.

13 Claims, No Drawings

PROCESS FOR PREPARING CARBAMAZEPINE FROM IMINOSTILBENE

The present invention relates to an improved process for preparing an N-carboxamido-dibenzazepine, particularly carbamazepine, from iminostilbene.

Carbamazepine, or 5-carbamoyl-5H-dibenz(b,f)azepine, is a known muscle relaxant/anticonvulsant eg antiepileptic and psychotropic drug, described in, inter alia, U.S. Pat. No. 2,948,718. The compound is also known as N-carbamoyliminostilbene, and various processes for preparing it from iminostilbene (hereinafter referred to as 'ISB') have been described.

For example, European patent specification no. 29 409 discloses the preparation of carbamazepine by reacting ISB with a halocyanogen to produce the 5-cyano derivative, followed by hydrolysation. However, this is an inconvenient 2-stage process that involves the use of toxic reagents. To try to overcome these disadvantages, persons skilled in the art have attempted other methods.

For example, European patents specifications nos. 277 095 and 688 768 disclose the reaction of ISB with cyanic acid (HOCN), which may be generated in situ, in an organic solvent in the presence of an acidic agent. An alternative method is disclosed in European patent specification no. 423 679, which relates to the chlorocarbonylation and subsequent ammonolysis of ISB; similarly, European patent specification no. 485 685 relates to the use of phosgene. These, and other known alternatives, also involve two process steps and/or toxic reagents.

All the known methods therefore suffer from disadvantages, in particular, the requirement to use 'environmentally-unfriendly' reactants, but we have surprisingly found that reaction of urea with a protonated form of ISB enables the disadvantages of the prior art to be overcome.

Accordingly, the present invention provides a process for the preparation of carbamazepine, which process comprises reacting, in a protonating medium, iminostilbene or a salt thereof with urea (of formula $H_2NCONH_2$) or a salt thereof. In this way, there is provided a single-step process that can be carried out at moderate temperatures at atmospheric pressure and that requires the use of only 'environmentally-friendly' reagents.

The protonating medium is one that allows protonation of the ISB and/or the urea in the reaction. Preferably, it allows proton transfer from the ISB to the urea. For example, the protonating medium may comprise a polar organic solvent and at least a catalytic amount of proton-donor that can donate a proton to the ISB. Preferably, the proton-donor is an inorganic acid, such as a mineral acid, eg sulphuric, hydrochloric or phosphoric acid. The preferred proton donor is sulphuric acid.

Conveniently, the ISB and proton donor may be present as the corresponding salt of ISB. For example, the process may comprise reaction of a mineral acid salt of ISB, such as ISB.HCl, ISB.$H_2SO_4$ or ISB.$H_3PO_4$, with the urea in a polar organic solvent. Alternatively, the urea and proton donor may be present as the corresponding salt of urea. For example, the process may comprise reaction of a mineral acid salt of urea, such as urea.HCl or urea.$H_2SO_4$, etc, with the ISB in a polar organic medium. Preferred ISB or urea salts are hydrochlorides.

Preferably, the polar organic solvent is an organic acid, such as an aliphatic carboxylic acid, preferably a $C_{1-4}$ carboxylic acid, most preferably acetic acid.

Preferably, the molar ratio of ISB:urea used in the reaction is in the range of from 1: about 10–about 14 (moles), more preferably about 1: 12–14 (moles).

As well as overcoming the disadvantages of the prior art methods, the process of the present invention provides further advantages in that the preparation of carbamazepine proceeds in near-quantitative yields, and is particularly suitable for large-batch production.

The reaction may be carried out at moderately elevated temperatures (at atmospheric pressure), such as in the range of from about 40° to about 100° C., preferably in the range of from about 80° to about 90° C., more preferably from about 80–85° C. The reaction may be completed during a period in the range of from about 4 to about 14 hours, preferably in the range of from about 6 to about 8 hours, such as from about 7 to about 8 hours.

Once complete, the reaction mixture may be diluted with water to precipitate the carbamazepine, which may then be separated from the mother liquor by filtration, followed by standard washing and drying procedures.

By analogy, therefore, the present invention further provides a process for the preparation of analogues or derivatives of carbamazepine, which process comprises reaction of a corresponding 5- or N-decarbamoyl derivative thereof with urea. The present invention therefore still further provides a process for the preparation of an N-carboxamido-cyclic secondary amine, which process comprises reaction of the corresponding cyclic secondary amine with urea.

The present invention further surprisingly provides the use of urea or a salt thereof in the preparation of a cyclic secondary amide, particularly carbamazepine, in particular, in the presence of a protonating medium, such as urea (base) in the presence of a proton donor, eg a catalytic amount of a mineral acid.

The carbamazepine, or analogue or derivative thereof, thereby prepared, may then be formulated, for example, by bringing it into association with a suitable carrier therefor, into a pharmaceutical formulation, as is known in the art.

The present invention will now be illustrated by the following non-limiting examples.

EXAMPLE 1

Preparation of Carbamazepine—Sulphuric Acid Catalyst

To a suspension of urea (400 g, 6.66 mols) in acetic acid (500 ml), sulphuric acid (15 ml) was added, followed by iminostilbene (100 g, 0.518 mols), under stirring at 25–30° C. The resulting reaction mixture was heated to 80–85° C. and maintained for a period of 7–8 hours, and the reaction was monitored by thin layer chromatography (TLC). The reaction mass was diluted with water, and the resulting carbamazepine product (m.p. 188–189° C.) separated by filtration, washed with water until neutral and dried at 90–100° C. until constant weight. The identity of the product was further verified by tlc (toluene/methanol 18/03, uv=254 nm) to be identical to the reference compound and by infra-red spectroscopy (KBr) $V_{max}$=3466, 1677, 1605, 1595 $cm^{-1}$.

EXAMPLE 2

Preparation of Carbamazepine—Phosphoric Acid Catalyst

To a suspension of urea (80 g, 1.333 mols) in acetic acid (100 ml), phosphoric acid (8 ml) was added, followed by iminostilbene (20 g, 0.103 mols), under stirring at 25–30° C. The resulting reaction mixture was worked up according to the method of Example 1 to produce carbamazepine, which was identical to the product of Example 1.

EXAMPLE 3

Preparation of Carbamazepine using ISB.HCl

To a suspension of urea (80 g, 1.333 mols) in acetic acid (100 ml), iminostilbene hydrochloride (20.5 g, 0.089 mols)

was added under stirring at 25–30° C. The resulting reaction mixture was worked up according to the method of Example 1 to produce carbamazepine, which was identical to the product of Example 1.

EXAMPLE 4

Preparation of Carbamazepine using Urea.HCl

To a suspension of urea hydrochloride (100 g, 1.036 mols) in acetic acid (125 ml), iminostilbene (25 g, 0.129 mols) was added under stirring at 25–30° C. The resulting reaction mixture was worked up according to the method of Example 1 to produce carbamazepine, which was identical to the product of Example 1.

What we claim is:

1. A process for the preparation of, which process comprises reaction, in a protonating medium, of the corresponding cyclic secondary amine with urea.

2. A process according to claim 1, wherein the reaction is carried out at a temperature in the range of from about 40° to about 100° C.

3. A process according to claim 1, wherein the reaction is carried out at a temperature in the range of from about 80° C. to about 90° C.

4. A process for the preparation of carbamazepine, which process comprises the reaction of iminostilbene (ISB) or a salt thereof with urea or a salt thereof in a polar organic solvent and at least a catalytic amount of a mineral acid.

5. A process for the preparation of carbamazepine, which process comprises reacting in a protonating medium, iminostilbene or a salt thereof with urea of the formula $H_2NCONH_2$ or a salt thereof.

6. A process according to claim 5, wherein the protonating medium comprises a polar organic solvent and at least a catalytic amount of a proton-donor that can donate a proton to the ISB.

7. A process according to claim 5, wherein the proton donor comprises an inorganic acid.

8. A process according to claim 5, wherein the proton donor comprises an inorganic acid selected from the group consisting of sulphuric, hydrochloric and phosphoric acids.

9. A process according to claim 5, wherein the ISB and proton donor are present as the corresponding salt of ISB, and/or the urea and proton donor are present as the corresponding salt of urea.

10. A process according to claim 5, wherein the polar organic solvent is an organic acid.

11. A process according to claim 5, wherein the polar organic solvent is acetic acid.

12. A process according to claim 5, wherein the reaction is carried out at a temperature in the range of from about 40° C. to about 100° C.

13. A process according to claim 5, wherein the reaction is carried out at a temperature in the range of from about 80° C. to about 90° C.

* * * * *